United States Patent [19]

Sharp

[11] Patent Number: 5,451,161
[45] Date of Patent: Sep. 19, 1995

[54] OSCILLATING CIRCUIT FOR ULTRASONIC DENTAL SCALER

[75] Inventor: Michael Sharp, Centerport, N.Y.

[73] Assignee: Parkell Products, Inc., Farmingdale, N.Y.

[21] Appl. No.: 110,857

[22] Filed: Aug. 24, 1993

[51] Int. Cl.$^6$ .................. A61C 1/07; A61C 3/03; A61C 3/08
[52] U.S. Cl. ................................................ 433/119
[58] Field of Search .................. 433/118, 119; 601/2, 601/46, 47, 48

[56] References Cited

U.S. PATENT DOCUMENTS

| | | | |
|---|---|---|---|
| 3,573,663 | 4/1971 | Huge et al. | 331/117 |
| 3,809,977 | 5/1974 | Balamuth et al. | 433/119 X |
| 3,828,770 | 8/1974 | Kuris et al. | |
| 4,249,901 | 2/1981 | Wieser | 433/119 |
| 4,734,658 | 3/1988 | Bohan, Jr. | 331/117 |
| 4,820,152 | 4/1989 | Warrin et al. | 433/119 X |
| 5,042,460 | 8/1991 | Sakurai et al. | 601/2 |
| 5,151,085 | 9/1992 | Sakurai et al. | 601/2 X |
| 5,180,363 | 1/1993 | Idemoto et al. | 601/2 X |

FOREIGN PATENT DOCUMENTS

| | | |
|---|---|---|
| 0454188A2 | 10/1991 | European Pat. Off. . |
| 2336912 | 7/1977 | France ................ 433/119 |
| 2929646 | 2/1981 | Germany ............ 433/119 |
| 3136028 | 3/1983 | Germany ............ 433/119 |
| 3739009 | 9/1988 | Germany ............ 433/119 |

*Primary Examiner*—Nicholas D. Lucchesi
*Attorney, Agent, or Firm*—Hoffmann & Baron

[57] ABSTRACT

A method and apparatus for vibrating a dental scaler insert at its resonant frequency which includes an energizing coil and an automatically tuned oscillating circuit is disclosed. The oscillating circuit is automatically tuned to vibrate a scaler insert at its resonant frequency in response to an impedance of the energizing coil. The energizing coil impedance is responsive to a scaler insert positioned within the energizing coil. Additionally, the dental scaler device can be operated with scaling inserts having different mechanical resonant frequencies associated therewith. Accordingly, dental scaler inserts resonant at about 25kHz or 30kHz may be inserted and operated by the dental scaler device of the present invention. The apparatus for vibrating a dental scaler may also include a feature permitting the operator to temporarily increase an amplitude of vibration of the scaler insert to enable the operator to dislodge stubborn calculus from a patient's teeth.

27 Claims, 4 Drawing Sheets

OSCILLATING CIRCUIT FOR ULTRASONIC DENTAL SCALER

BACKGROUND OF THE INVENTION

1. Field of the Invention

The present invention relates generally to ultrasonic dental scalers, and more particularly relates to an oscillating circuit for vibrating a dental scaler insert tip at its ultrasonic resonant frequency.

2. Description of the Prior Art

It is known in the art to clean calculus from teeth using an ultrasonic dental scaler. Generally, in an ultrasonic dental scaler, vibrational motion of a transducer is transformed to flexural or elliptical motion of a dental scaler insert tip. Common frequencies of operation are 25 kHz and 30 kHz, although frequencies as low as 18 kHz and as high as 40 kHz have been used. The vibratory motion of the scaler insert tip is used to dislodge calculus from the teeth of a patient. In most cases, the scaler also includes a means for irrigating the area around the scaler tip by dispensing a liquid, such as water, through or over the surface of the scaler tip.

Magnetostrictive ultrasonic dental scalers usually include a dental handpiece having an ultrasonic transducer positioned within an energizing coil located within a sleeve. The transducer or scaler insert conventionally comprises a stack of laminar plates of magnetostrictive material that is excited by the energizing coil to longitudinally expand and contract the transducer at an operational resonant frequency. Conventional dental scalers are designed to operate at one specific frequency, usually 25 kHz or 30 kHz. Thus, a dentist would need to have two dental scaler devices in order to be able to use scaling inserts having different resonant frequencies. This is usually impractical due to space limitations as well as cost factors. Accordingly, the dentist is forced to choose a resonant frequency of operation and can only use scaling inserts having the chosen resonant frequency.

To properly vibrate the scaler insert, the electronic circuit generally includes an oscillating circuit having a variable output amplitude. The frequency of the oscillator is adjusted to the mechanical resonance of the scaling insert. Traditionally, this adjustment or tuning was achieved by either a manually tuned circuit adjusted by the dentist for optimum vibration or automatically using a feedback coil in the handpiece coupled to associated control circuitry to electronically adjust a variable frequency oscillator to the correct output frequency.

The feedback coil is generally formed by winding a very fine wire near the base of the handpiece. The feedback coil of fine wire is provided to register a voltage developed by the movement of the ultrasonic scaler insert within the electro-magnetic field of the handpiece. Associated control circuitry uses this information to electronically adjust the variable frequency oscillator to the correct output frequency. The feedback coil tends to be very fragile due to the fine gauge wire from which it is formed. Additionally, the feedback coil requires that an extra conductor be placed in the handpiece cable coupling the feedback coil at the base of the handpiece to the device electronics located in a separate housing. Thus, the feedback coil tends to be a common source of malfunction or failure of conventional dental scalers.

Conventional dental scalers also include a power setting to allow the dentist to adjust the power or amplitude of vibration depending upon the needs of the dentist during the cleaning procedure. During the removal of calculus, it may be necessary to increase the power to the scaler tip to break the calculus from the tooth surface. This power setting is most commonly performed by turning a power adjustment knob located on the housing containing the electronic circuit. Once the stubborn piece of calculus is removed, the power must again be adjusted to a lower setting to provide adequate cleaning power and for patient comfort. Consequently, the dentist may have to adjust the power setting several times during a cleaning procedure. The necessary adjustments are time consuming and prolong the cleaning procedure. It would therefore be advantageous to have a means for quickly adjusting the power setting of the dental scaler to suit the needs of the dentist.

Thus, the present invention is directed toward overcoming the disadvantages of conventional dental scalers which have been discussed above.

OBJECTS AND SUMMARY OF THE INVENTION

It is an object of the present invention to provide a dental scaler having an oscillating circuit which is automatically tuned to the resonant frequency of oscillation of the scaling insert without the use of a fine wire feedback coil in the handpiece.

It is a further object of the present invention to provide a dental scaler having an oscillating circuit which is capable of vibrating scaler inserts which operate at different resonant frequencies.

It is yet a further object of the present invention to provide an oscillating circuit for a dental scaler having a convenient, simple means for temporarily increasing the power or amplitude of vibration of the dental scaler tip without adjusting a power control knob of the dental scaler device.

In accordance with one form of the present invention, an apparatus for use with a dental scaler insert having a resonant frequency associated therewith includes a handpiece, a coil mounted within the handpiece, a cavity within the handpiece and extending through the coil, the cavity being adapted for receiving a scaler insert, an oscillating circuit coupled to the coil for providing power to the coil and power supply means coupled to the oscillating circuit such that, when the coil is energized by the oscillating circuit, a scaler insert positioned within the cavity alters the impedance of the coil, the coil impedance automatically tuning the oscillating circuit to cause the insert to vibrate substantially at its resonant frequency. Thus, the present invention provides an apparatus which automatically tunes the frequency of oscillation of the scaler insert to its mechanical resonant frequency.

The apparatus formed in accordance with the present invention is also capable of operating with dental scaler inserts having different resonant frequencies of operation. For example, a scaler insert having approximately either a 25 kHz or a 30 kHz resonant frequency may be vibrated using the apparatus described above. The apparatus preferably includes a means for setting at least a first and second frequency range of oscillation. Conventional dental scalers are designed to operate dental scaler inserts having the same approximate resonant frequency of oscillation. Accordingly, an operator would require a dental scaling device for each different frequency of operation of various dental scaler inserts.

The apparatus of the present invention permits the operator to select a scaler insert having the optimum frequency range of operation dependent upon the particular patient's needs, as well as the operator's own personal preferences.

The apparatus of the present invention may also include a means for temporarily increasing the output power of the oscillating circuit to temporarily increase an amplitude of vibration of the scaler insert. A temporary increase in the amplitude of vibration may be necessary during the scaling procedure to dislodge stubborn calculus from the surface of the teeth being cleaned. The means for increasing the output power is preferably in the form of a push-button switch which is easily activated and deactivated. Furthermore, the power may be temporarily increased as a percent difference between an original power setting and a full power setting.

The present invention is also directed to an ultrasonic dental scaler including a handpiece adapted for removably receiving a dental scaler insert, an energizing coil having a first impedance mounted on the handpiece and adapted for surrounding a scaler insert removably positioned on the handpiece and a means for oscillating the scaler insert. The oscillating means provides power to the energizing coil to vibrate the insert. The energizing coil has a second impedance in response to a scaler insert positioned within the energizing coil such that the oscillating means is automatically tuned to vibrate the scaler insert at its mechanical resonant frequency in response to the second impedance of the energizing coil. The oscillating means preferably includes a power supply means and an oscillating circuit coupled to the power supply means. The oscillating circuit includes a transistor oscillator which provides alternating voltage to the energizing coil to vibrate the 35 scaler insert positioned within the coil.

The oscillator circuit also preferably includes a protection circuit which limits the current provided to the oscillating circuit to a predetermined value. The protection circuit may include detection means for detecting current flowing in the oscillating circuit and a transistor such that current to the oscillator circuit is limited by the detective means providing feedback to said transistor.

A method of vibrating a dental scaler insert using a dental scaler device formed in accordance with the present invention includes the steps of providing a dental scaler device having the features previously described and inserting a dental scaler insert within the energizing coil such that the impedance of the energizing coil is altered in response to the dental scaler insert whereby the oscillating means is automatically tuned to the resonant frequency of oscillation of the scaler insert in response to the energizing coil impedance. Since the dental scaler device formed in accordance with one form of the present invention can vibrate scaler inserts having different resonant frequencies of oscillation, the method may also include selecting a scaler insert and positioning a means for setting at least a first and second frequency of oscillation of the oscillating means to correspond to the scaler insert selected thereby setting the correct values of the oscillating means to vibrate the dental scaler at its resonant frequency of oscillation. Furthermore, the method may include the steps of providing and operating a means for temporarily increasing the amplitude of vibration of a scaler insert to dislodge stubborn calculus from a patient's teeth.

In its broadest sense, the present invention is directed to an ultrasonic dental scaler including a handpiece adapted for removably receiving a dental scaler insert, energizing means on the handpiece selectively positioned with respect to a dental scaler insert received by the handpiece and means for oscillating the scaler insert. The oscillator means provides power to the energizing means. The energizing means is responsive to the selective positioning of the dental scaler insert received by the handpiece such that the oscillating means is automatically tuned to vibrate the dental scaler insert at a resonant frequency in response to the energizing means. The present invention is also directed to a method of vibrating a dental scaler insert including providing a dental scaler device as described above and inserting a dental scaler insert into the handpiece so that the oscillating means is automatically tuned to the resonant frequency of operation of the inserted dental scaler insert.

A preferred form of the dental scaler device and associated oscillating circuit, as well as other embodiments, objects, features and advantages of this invention, will be apparent from the following detailed description of illustrative embodiments thereof, which is to be read in connection with the accompanying drawings.

DETAILED DESCRIPTION OF THE PREFERRED EMBODIMENTS

Figure 1:
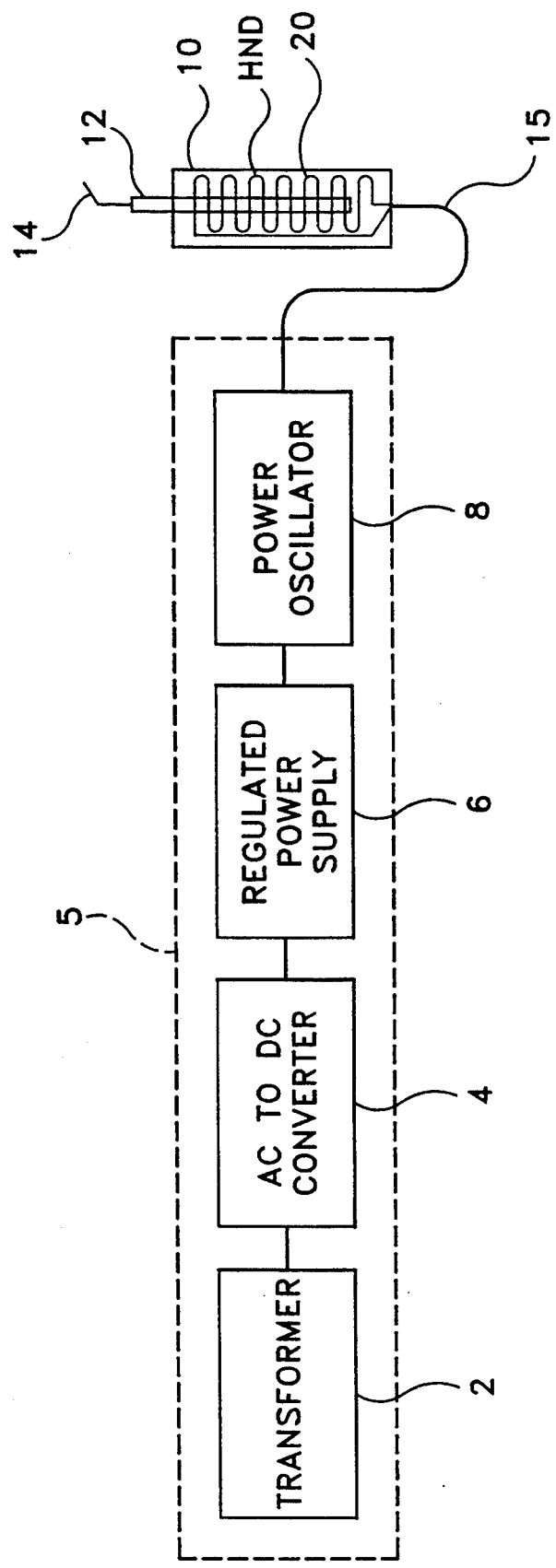
FIG. 1 is a block diagram of an electronic circuit for vibrating a dental scaler insert formed in accordance with the present invention.

A block diagram of an electronic circuit formed in accordance with the present invention is illustrated in FIG. 1. The electronic circuit preferably includes the following major sections: a voltage reducing transformer 2, an AC to DC converter 4, a regulated power supply 6 and a power oscillator circuit 8 including an energizing coil 20 positioned within a handpiece of the dental scaler device. The dental scaler device includes a housing 5 and a handpiece 10 coupled to the housing by a flexible cable 15. The transformer 2, AC to DC converter 4, regulated power supply 6 and power oscillator 8, excluding the energizing coil in the handpiece 10, are mounted within the housing 5. The energizing coil in the handpiece 10 is coupled to the power oscillator circuit by conductors positioned within the flexible cable 15 connecting the handpiece 10 to the housing 5. The handpiece 10 is adapted for removably receiving a scaler insert 12. The dental scaler insert 12 is provided with a scaling tip 14 which is ultrasonically vibrated by the oscillating circuit. The scaler tip 14 is placed in contact with a patient's teeth during scaling procedures. The dental scaler device may also include a means for irrigating the areas around the scaler tip 14 by dispensing a liquid, such as water, through or over the surface of the scaler tip 14. The water also provides cooling to the magnetostrictive scaler insert 12 being vibrated in the handpiece 10.

The transformer 2 includes an input coupled to a standard AC power supply i.e., 117 volts AC in the United States. The transformer 2 reduces the voltage to approximately 25 volts AC under load and also provides isolation to the electronic circuit formed in accordance with the present invention. The output of the transformer 2 is coupled to an AC to DC converter 4 which converts the low voltage AC to a DC voltage. The AC to DC converter 4 rectifies and smoothes the low voltage AC supplied by the transformer 2 to provide a DC voltage supply to the remainder of the electronic circuit. The output of the AC to DC converter 4 is coupled to a regulated power supply 6. In the preferred embodiment, the regulated power supply is a switching regulated power supply. The switching regulated power supply is used to reduce the heat dissipation in the transistor of the voltage regulator. The operation of the switching regulated power supply will be described later in greater detail.

The switching regulated power supply 6 is coupled to the power oscillator circuit 8 which preferably includes a single transistor oscillator. The power oscillator portion of the circuit is quite different from conventional feedback oscillator circuits presently used in dental scaling devices. The power oscillator formed in accordance with the present invention includes the unique feature that the resonant frequency of the oscillator is set by the energizing coil 20 which is part of the collector circuit of the transistor oscillator. The coil 20 is positioned within a handpiece cavity adapted to removably receive a dental scaler insert. When a scaler insert is positioned within the handpiece cavity, the energizing coil surrounds the scaler insert. The scaler insert has associated with it a mechanical resonant frequency based upon the length of the magnetostrictive stack of the insert.

In the power oscillator portion of the circuit formed in accordance with the present invention, the scaler insert is made part of the resonant circuit and the component values in the power oscillator circuit are selected so that the circuit will tend to oscillate at the mechanical resonant frequency of the scaler insert. More specifically, the circuit includes a switch which allows the circuit to be adjusted to properly compensate for scaler inserts which are preferably resonant at about 25 kHz and inserts resonant at about 30 kHz, although other frequencies can be selected. Furthermore, the oscillator circuit is automatically tuned to oscillate at the resonant frequency of the scaler insert in response to an impedance of the energizing coil. The power oscillator circuit will be described in greater detail with respect to FIG. 3.

Figure 2:
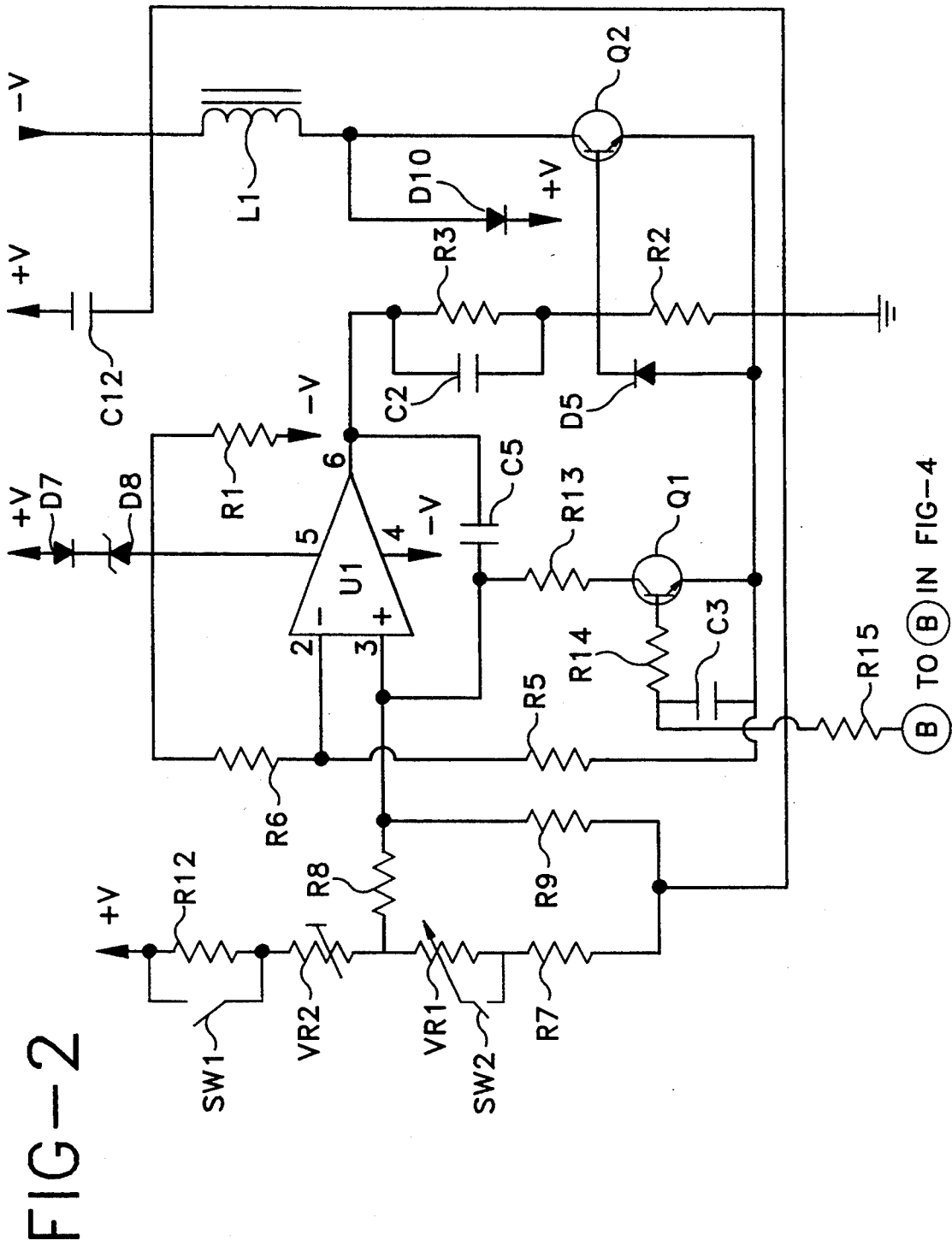
FIG. 2 is a schematic diagram of a switching regulated power supply formed in accordance with the present invention.

FIG. 2 is a schematic diagram of a regulated power supply formed in accordance with the present invention. The illustrated power supply is a switching regulated power supply which is coupled to the output of the voltage reducing transformer 2 (not shown) as previously described with reference to FIG. 1. The positive input terminal for the switching regulated power supply is coupled to diodes D7, D8 which together reduce the voltage applied to operational amplifier U1 to provide the correct voltage to U1. The circuit including diodes D7, D8 tends to improve regulation of line voltage fluctuations. The cathode of diode D8 is also coupled through a resistor R6 to the inverting input of operational amplifier U1 at pin 2. One end of resistor R6 is also coupled to one end of resistor R5 forming a voltage divider and providing a reference potential at the inverting input of operational amplifier U1 (pin 2 ).

The non-inverting input of operational amplifier U1 (pin 3) is also coupled to a voltage divider network. The voltage divider network includes resistor R12 coupled in parallel with a first pole of switch SW1, connected to potentiometer VR2. Switch SW1 is a single-throw, double-pole toggle switch. The second half of the voltage divider is formed from a parallel network including a potentiometer VR1 coupled in series with resistor R7 and a push-button switch SW2 connected between potentiometer VR1 and resistor R7. Resistor R9 is coupled in parallel with the previously described series network including potentiometer VR1. The voltage divider including VR1 and VR2 is coupled through resistor R8 to the non-inverting input of operational amplifier U1.

The output of operational amplifier U1 (pin 6) is fed through a network which includes a capacitor C2 coupled in parallel with resistor R3, the parallel network being connected to a network including resistor R2 coupled in parallel with diode D5. This network is used to condition the output of operational amplifier U1 and drive transistor Q2. The output of operational amplifier U1 is also fed back through capacitor C5 into the non-inverting input of operational amplifier U1 at pin 3.

The switching regulated power supply also includes a power transistor Q2 having its base coupled to the juncture between the parallel networks including R3, C2 and diode D5 and resistor R2. The emitter of transistor Q2 is coupled to ground. The collector of transistor Q2 is coupled to one end of an inductor L1. The other end of inductor L1 is coupled to the parallel network including potentiometer VR1. One end of inductor L1 is also the negative output terminal for the switching regulated power supply. A diode D10 is tapped into the collector circuit between the transistor collector and the inductor L1 at its cathode and its anode is connected to the positive terminal of the power supply. The terminal end of inductor L1 is also tapped into a capacitor C12 having its other end coupled to the positive terminal of the power supply.

Referring to FIG. 2, the switching regulated power supply also preferably includes a protection circuit. The protection circuit includes a transistor Q1 having its collector coupled through resistor R13 to the feedback loop connected to the non-inverting input (pin 3) of operational amplifier U1. The emitter of transistor Q1 is coupled to the feedback loop connected to the non-inverting input of operational amplifier U1. The base of transistor Q1 is coupled to a resistor R14 having its other end connected to a capacitor C3. A juncture of capacitor C3 and resistor R14 is also coupled through resistor R15 to the remainder of the protection circuit illustrated in FIG. 4.

Figure 3:
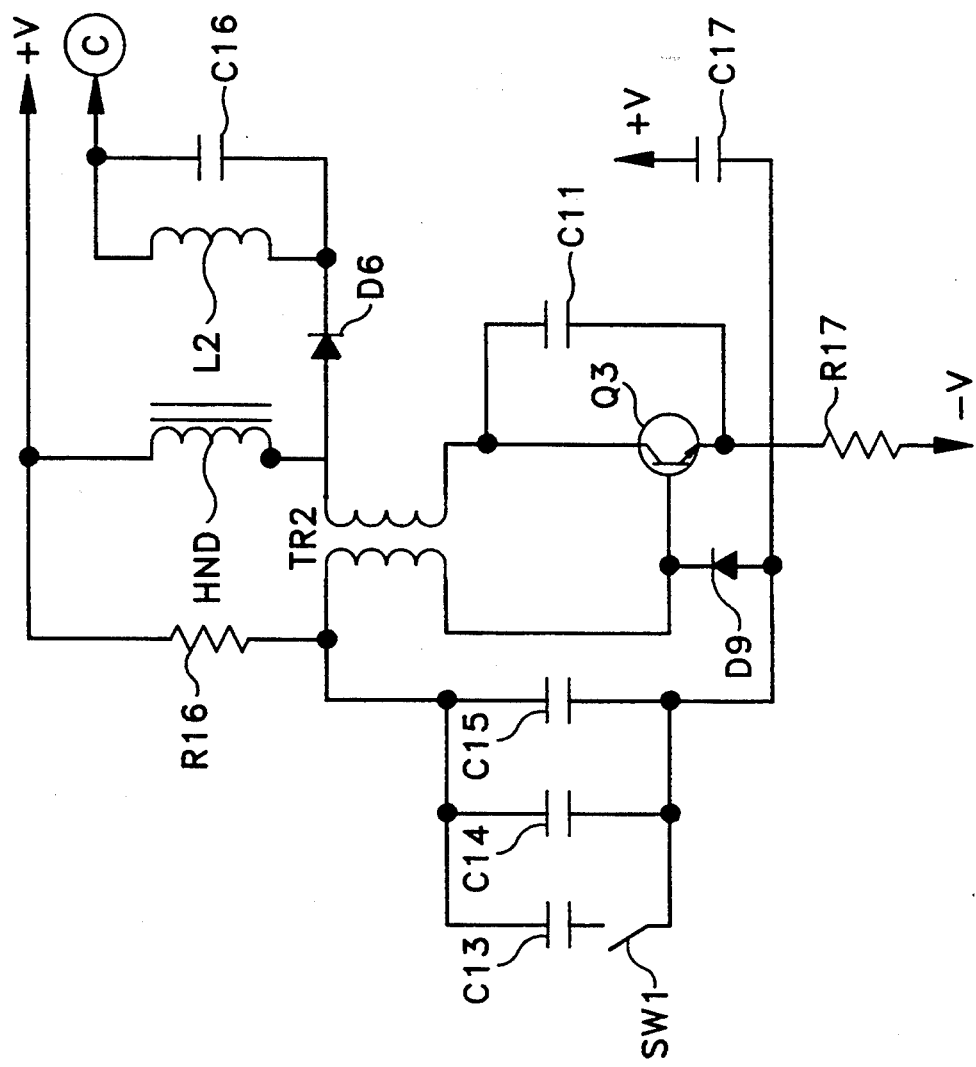
FIG. 3 is a schematic diagram of an oscillating circuit formed in accordance with the present invention.

Referring now to FIG. 3, a schematic of the power oscillator circuit formed in accordance with the preferred embodiment of the present invention is illustrated. The power oscillator circuit includes a transistor Q3 having feedback between the base and collector circuits provided by a transformer TR2. More specifically, the base of transistor Q3 is coupled to one end of the primary winding of transformer TR2. The other end of the primary winding is coupled to a parallel capacitor network including capacitors C13, C14 and C15. A second pole of switch SW1 is connected in series with capacitor C13 thereby permitting a total capacitance of the parallel network to be adjusted in response to the switch position. The opposite end of the parallel capacitive network is coupled to the emitter of transistor Q3. Additionally, a diode D9 is connected having its anode coupled to the base of transistor Q3 and its cathode is coupled to the emitter of transistor Q3. Furthermore, a capacitor C11 is connected across the transistor Q3 from the collector to the emitter.

The collector of transistor Q3 is also connected to one end of the secondary winding of transformer TR2. The other end of the secondary winding of transformer TR2 is connected to one end of an energizing coil, designated in the schematic as HND, which is a coil formed in the handpiece of the dental scaler device which surrounds a magnetostrictive scaling insert. The other end of the coil HND is coupled to the positive terminal of the voltage supply along with resistor R16 whose other end is coupled to the primary winding of transformer TR2. Additionally, a parallel network used to absorb flyback energy from the coil HND in the handpiece includes an inductor L2 connected in parallel with a capacitor C16, the network being coupled through a diode D6 to the secondary winding of transformer TR2. The diode D6 is connected so that its cathode is connected to the secondary winding of the transformer TR2 and the anode connected to one end of the parallel network formed by L2 and C16. The opposite end of the parallel network is connected to the protection circuit at point C shown in FIG. 4. The other end of the coil HND is coupled to the positive output terminal of the AC to DC converter.

The emitter of transistor Q3 is coupled to the negative output terminal of the switching regulated power supply through a resistor R17 having its other end coupled to inductor L1 of the power supply. The emitter of transistor Q3 is also coupled to a capacitor C17 which also acts to regulate the power to transistor Q3.

Figure 5:
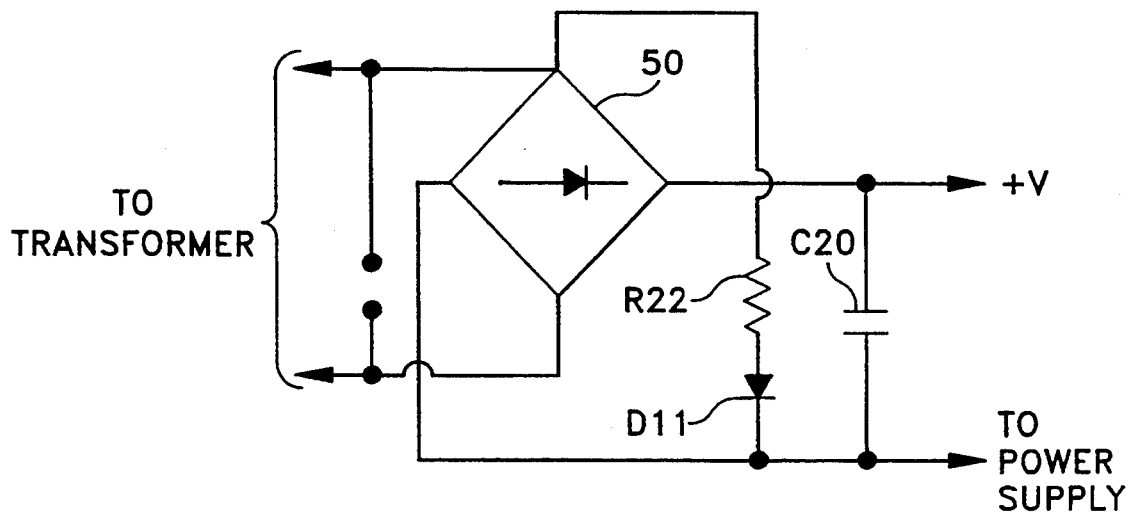
FIG. 5 is a schematic diagram of an AC to DC converter formed in accordance with the present invention.

An AC to DC converter for use in the circuit formed in accordance with the present invention is illustrated schematically in FIG. 5. The AC to DC converter is coupled to the secondary winding of a voltage reducing transformer as shown with reference to FIG. 1, which interfaces the circuit to a standard AC voltage supply. The transformer provides a voltage of approximately 25 volts AC to the AC to DC converter. The DC converter may be formed from any known design. Preferably, the AC to DC converter is formed using a bridge rectifier circuit 50. The circuit preferably includes a light emitting diode (LED) D11 to indicate that the power to the unit is on. Furthermore, the AC to DC converter includes a capacitor C20 to further smooth the output voltage. The output of the AC to DC converter is coupled to the input of the power supply schematically illustrated in FIG. 2.

The operation of the circuit formed in accordance with the present invention to oscillate a dental scaling insert at its mechanical resonant frequency will now be described in detail in reference to the Figures. As previously described, with respect to FIG. 1, a voltage reducing transformer interfaces the dental scaler unit to a standard AC power supply. The transformer provides isolation and reduces the voltage to approximately 25 volts AC under load. The output voltage from the transformer is input to an AC to DC converter which rectifies and smoothes the low voltage AC supplied by the transformer. The AC to DC converter provides a DC voltage to the regulated power supply used to operate the circuit.

The operation of regulated power supply is described with reference to FIG. 2. In the illustrated switching regulated power supply of the present invention, diode D7 and zener diode D8 reduce the voltage from the AC to DC converter to a voltage which is useful for operating the operational amplifier integrated circuit U1. A voltage divider formed by resistors R5 and R6 sets a reference voltage for the inverting input of operational amplifier U1 at pin 2. The operational amplifier U1 operates as a comparator and compares the fixed reference voltage from the voltage divider formed by resistors R5 and R6 with feedback voltage from the output of the inductor L1 through a voltage divider network of including potentiometers VR1 and VR2. The non-inverting input of operational amplifier U1 is provided with a reference voltage through the voltage divider network including resistors R12, VR2, VR1, R7, R9 and R8. Additionally, the voltage divider network including potentiometers VR1 and VR2 is connected to the output of the switching regulated power supply.

Potentiometer VR2 provides an internal preset which is used to set up the basic operating conditions of the circuit. Potentiometer VR1 is adjustable by the operator of the device and adjusts the output voltage at the negative output terminal of the power supply. By adjusting potentiometer VR1 and thus adjusting the output voltage or power to the circuit, the amplitude of oscillation of the scaling insert can be controlled by the operator. Potentiometer VR1 is preferably in the form of a variable power control knob located on the housing of the dental scaling device. Additionally, push-button switch SW2 is also provided to adjust the output voltage of the power supply. The push-button switch SW2 provides the operator of the dental scaling device with a means for temporarily increasing the power or amplitude of vibration of the scaling insert in order to remove stubborn calculus from the teeth of a patient. More specifically, the push-button SW2 may increase the power by a percentage of the difference between the present power setting and a full power setting. The original operating setting is easily restored by simply operating the push-button switch SW2 when the increased power is no longer needed.

Furthermore, the power supply is provided with an external switch SW1 which can be operated to adjust the circuit for different scaling inserts having a different frequency of operation. Since the electronic circuit and handpiece of the dental scaler formed in accordance with the present invention can operate with scaling inserts having different mechanical resonant frequencies, the switch SW1 provides the circuit with a means for setting at least a first and second frequency range of oscillation. More specifically, the first pole of switch SW1 shunts resistor R12 when the higher frequency scaling insert is being used, and is an open circuit such that the output voltage flows through a current limiting resistor R12 when a lower frequency dental scaling insert is being used. The second pole of switch SW1 is used to alter the capacitance in the base circuit of the transistor Q3 on the power oscillator circuit thereby adjusting the voltage supplied to the handpiece coil. It is also envisioned that the circuit may be automatically adjusted depending upon the resonant frequency of the scaler insert positioned in the handpiece.

The capacitor C5 of the regulated power supply is provided in a feedback loop between the output of operational amplifier U1 and pin 6 and the non-inverting input at pin 3 of operational amplifier U1 to provide hysteresis or a time constant to the operational amplifier. Accordingly, capacitor C5 ensures that the operational amplifier has a basic minimum time period during which it can be switched on or off. Also coupled to the output (pin 6) of operational amplifier U1 is a network including a voltage divider formed by resistors R2 and R3 and a diode D5 connected in parallel with resistor R2. Capacitor C2 and diode D5 form a speed-up circuit. The speed-up circuit ensures that the pulse waves output from pin 6 of operational amplifier U1 are transmitted to the base of transistor Q2 without any loss in rise time.

Transistor Q2 of the regulated power supply is a switching element such as a Darlington power transistor. In operation, transistor Q2 switches on and off very quickly to provide an output voltage. Transistor Q2 tends to dissipate less energy than a linear power supply since the transistor is either fully on or fully off during operation, whereas the linear power supply in continuously on and therefore dissipates more energy. Diode D10 which is coupled to the collector of transistor Q2 provides flyback protection. Diode D10 reduces high voltage spikes which may be caused by switching the current through inductor L1. Inductor L1 and capacitor C12 are smoothing devices which regulate the voltage at the output of the switching regulated power supply so that the switching pulsed voltages output from power transistor Q2 are provided as a smooth voltage at the output of the switching regulated power supply.

Referring now to FIG. 3, the oscillator circuit preferably comprises a single transistor oscillator Q3 having a transformer TR2 which provides feedback from the collector of the oscillating transistor Q3 to the base. The transistor oscillator Q3 operates an oscillator providing the energizing coil HND in the handpiece with an AC voltage. The energizing coil HND excites the magnetostrictive scaler insert material to longitudinally expand and contract at an operational resonant frequency. Thus, the dental scaler tip which is coupled to the magnetostrictive transducer is vibrated at an ultrasonic frequency for use in teeth scaling procedures.

The parallel network of capacitors C13, C14 and C15 in the power oscillator circuit set the resonant frequency range over which the oscillator circuit will work. Capacitor C13 is connected in series with a second pole of switch SW1 such that capacitor C13 is switchable into and out of the capacitive network thereby adjusting the range of operating frequencies. Toggle switch SW1 allows the circuit of the preferred embodiment to be adjusted to properly compensate for scaler inserts resonant at about 25 kHz to about 30 kHz. Dependent upon the needs of the dentist, the circuit can be easily modified to operate at any other frequency that may be desirable. Accordingly, if another frequency or frequencies of operation are desired, capacitors C13, C14 and C15 can be chosen to have values specifically determined to operate the circuit at the desired frequency ranges for the scaling inserts being used. Thus, the dentist is not limited to using a single insert and can experiment with scaler inserts having different frequencies of operation to determine which frequency best suits the dentist's needs without purchasing two separate dental scaling units.

The resistor R16 is part of the base circuit of transistor Q3 and limits the amount of current flowing through the base circuit. Thus, when the transistor Q3 is operated in the linear region, the circuit will produce an alternating voltage in the energizing coil HND which will vibrate the scaling insert positioned within the energizing coil.

The frequency of oscillation is set by the energizing coil HND in the handpiece of the device formed in accordance with the present invention. The energizing coil HND in the handpiece is part of the resonant circuit and collector circuit of transistor Q3 and provides the frequency control for the power oscillator circuit. The frequency control or automatic tuning of the oscillating circuit is achieved in response to the scaling insert placed within the handpiece of the device and the positioning of switch SW1. The power oscillator circuit is automatically tuned to the correct frequency of oscillation to vibrate the scaling insert at its resonant frequency because the insert positioned within the coil HND affects the impedance of the energizing coil thus forming a frequency dependent element. The energizing coil impedance tends to adjust the oscillating frequency of the circuit to the mechanical resonant frequency of the scaling insert. The impedance of the coil affects the current in the collector circuit of the transistor oscillator and the feedback via transformer TR2 to the base circuit to automatically tune the output alternating voltage to vibrate the scaling insert at its resonant frequency. Accordingly, based upon the insert positioned within the energizing coil HND in the handpiece, the power oscillator circuit will be automatically tuned to the resonant frequency of the particular scaling insert in the circuit.

Connected to the emitter circuit of transistor Q3 are resistor R17 and capacitor C17. These elements further regulate the power of the circuit and provide a smoothing of the output voltages. Additionally, transistor Q3 has a diode D9 coupled between the emitter and base to ensure that excessive charge does not get stored on the base of the transistor Q3. The diode D9 maintains the voltage at the base so that it cannot go too far negative from the voltage at the emitter of transistor Q3. The network comprising diode D6, inductor L2 and capacitor C16 absorb flyback energy which may be generated by the energizing coil HND positioned within the handpiece.

Figure 4:
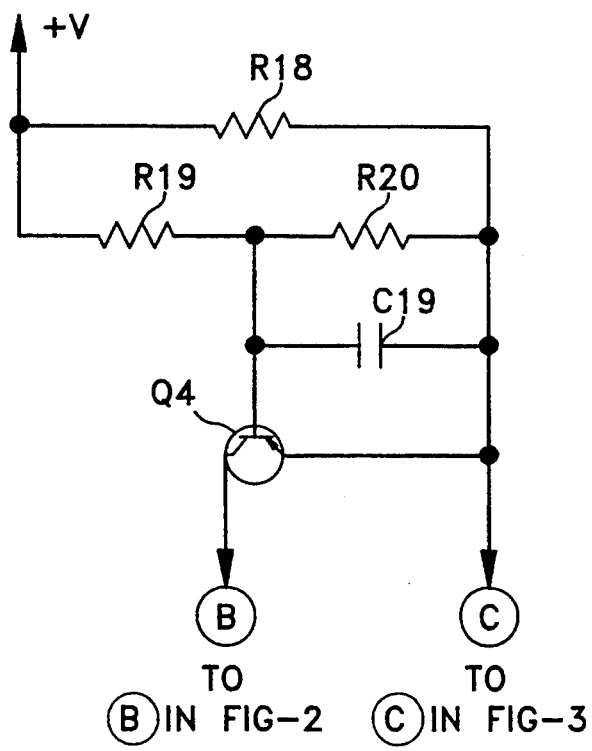
FIG. 4 is a schematic diagram of a protection circuit formed in accordance with the present invention.

The dental scaler device formed in accordance with one form of the present invention permits the user to change the scaling insert from either a 25 kHz insert to a 30 kHz insert. If the dentist were to remove the insert while the unit was operating, a current spike may be sent through the power oscillator circuit which may cause damage to the circuit. A fuse or some other similar device may be used to protect the circuit from the possibility of a current spike; however, a protection circuit is the preferred method of protecting the electronic components against a sudden increase in current. The preferred protection circuit for the power oscillator is illustrated in FIG. 4.

The protection circuit is connected to the power oscillator circuit at one end of the energizing coil HND in the handpiece, as well as being connected to the network including inductor L2, capacitor C16 and diode D6 of the power oscillator circuit. The protection circuit is also coupled to the switching regulated power supply through resistor R15. The protection circuit measures the current in the network including diode D6, inductor L2 and capacitor C16 to limit the amount of current which can flow through the oscillator circuit. The protection circuit operates by controlling the maximum current flowing into the power oscillator circuit by feedback to transistor Q1 in the regulated power supply circuit. Thus, if the protection circuit senses a sudden increase in current above a predetermined level, through feedback to transistor Q1 in the power supply, the voltage across the oscillator circuit is reduced and the current is thereby held in check.

As shown in FIG. 5, the AC to DC converter includes a bridge rectifier 50, a smoothing capacitor C20 and a current limiting resistor R22 connected in series with a light emitting diode D11 (LED) to indicate that the power supply is on. The AC to DC converter operates to convert the low voltage AC from voltage reducing transformer 2 to a DC voltage which is supplied to the regulated power supply.

Thus, the electronic circuit including the voltage reducing transformer, the AC to DC converter, the regulated power supply and the power oscillator circuit together form an oscillating means for vibrating a dental scaler insert at its resonant frequency.

A parts list for the circuit illustrated in FIGS. 2–5 is provided below. Additionally, the pin numbers shown in FIG. 3 for operational amplifier U1 relate to the part specified in the list. It is envisioned that components comparable to those listed below, connected differently from that shown in FIGS. 2–5, may be suitable to practice the invention.

| PARTS LIST FOR ELECTRONIC CIRCUIT ILLUSTRATED IN FIGS. 2–5 | |
|---|---|
| Resistor 4.7 kΩ | R1 |
| Resistor 1.5 kΩ | R2 |
| Resistor 4.7 kΩ | R3 |
| Resistor 330 kΩ | R5 |
| Resistor 10 kΩ | R6 |
| Resistor 100 Ω | R7 |
| Resistor 4.7 kΩ | R8 |
| Resistor 10 kΩ | R9 |
| Resistor 1 kΩ ¼ W MF | R12 |
| Resistor 100 Ω | R13 |
| Resistor 10 kΩ | R14 |
| Resistor 10 kΩ | R15 |
| Resistor 270 Ω 5w | R16 |
| Resistor 0.1 Ω | R17 |
| Resistor 0.27 Ω 5w | R18 |
| Resistor 1.5 kΩ | R19 |
| Resistor 1.5 kΩ | R20 |
| Resistor 4.7 kΩ | R22 |
| Potentiometer 5 k | VR1 |
| Potentiometer 2 k SVR | VR2 |
| Operational Amplifier (Part No. UA741) | U1 |
| Capacitor 0.01 μf | C2 |
| Capacitor 0.1 μf | C3 |
| Capacitor 4700 pf | C5 |
| Capacitor 2200 pf | C11 |
| Capacitor 220 μf | C12 |
| Capacitor 0.1 μf | C13 |
| Capacitor 0.1 μf | C14 |
| Capacitor 0.33 μf | C15 |
| Capacitor 330 μf | C16 |
| Capacitor 220 μf | C17 |
| Capacitor 0.01 μf | C19 |
| Capacitor 4700 μf | C20 |
| Diode 1N4148 | D5 |
| Diode MR918 | D6 |
| Diode 1N4004 | D7 |
| Diode 1N4739 | D8 |
| Diode 1N4004 | D9 |
| Diode 1N4004 | D10 |
| Diode (LED) | D11 |
| Inductor | L1 |
| Inductor | L2 |
| Transformer | TR2 |
| Switch - single-throw, double-pole toggle switch | SW1 |
| Switch - single-throw, single-pole push-button switch | SW2 |
| Transistor - Darlington MPSA13 | Q1 |
| Transistor - Darlington Power Transistor 6388 | Q2 |
| *-continued* | |
| PARTS LIST FOR ELECTRONIC CIRCUIT ILLUSTRATED IN FIGS. 2–5 | |
| Transistor - 2SC3281 | Q3 |
| Transistor - MPSA92 | Q4 |

The present invention is also directed to a method of vibrating a dental scaler insert such that the scaler insert is automatically tuned to vibrate at a resonant frequency to optimize dental scaling procedures. The method includes the use of a dental scaler device formed in accordance with the present invention as previously described. The method basically includes the steps of inserting a dental scaler insert having a scaling tip into the handpiece of the dental scaler device and causing the oscillating means of the dental scaler device to provide power to the energizing coil such that the dental scaler insert is vibrated at its resonant frequency of oscillation in response to the scaler insert. More specifically, the energizing coil has an initial first impedance associated therewith and a second impedance in response to the positioning of a dental scaler insert within the coil, the oscillating means being automatically tuned to the correct frequency of oscillation in response to the second impedance of the energizing coil.

Additionally, the method may include providing a means for temporarily increasing the amplitude of vibration of the scaler insert and operating the means for temporarily increasing the amplitude of vibration of the scaler insert to dislodge stubborn calculus from a patient's teeth. Furthermore, since the dental scaler device of the present invention can be used to vibrate scaler inserts having different resonant frequencies of operation, the method may include the steps of selecting a dental scaler insert, positioning a means for setting at least a first and second frequency of oscillation to correspond to the scaler insert selected and inserting the scaler insert within the energizing coil of the dental scaler device.

Thus, the oscillating circuit for use with a dental scaler device formed in accordance with the present invention overcomes the disadvantages of conventional dental scalers. The oscillating circuit of the present invention includes the desired feature of automatically tuning the circuit to operate at the resonant frequency of oscillation of the scaler insert positioned within the energizing coil.

Furthermore, the oscillating circuit is designed to work with at least two different scaling inserts having different resonant frequencies. More specifically, the dental scaler formed in accordance with the preferred embodiment can operate with scaling inserts having resonant frequencies of about 25 kHz and about 30 kHz at the flip of a switch. Additionally, the dental scaler device formed in accordance with the present invention includes a feature such that the power or amplitude of vibration can be quickly and easily temporarily increased at the touch of a button to enable the dentist to dislodge stubborn calculus. The setting can be returned to its original setting by once again pushing the button.

Thus, the oscillating circuit formed in accordance with the present invention provides a more reliable, more versatile method of vibrating a scaler insert at its resonant frequency. Moreover, the frequency of oscillation is automatically tuned to the resonant frequency of the scaler insert being used.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An apparatus for use with a dental scaler insert having a resonant frequency associated therewith, which comprises:
   a handpiece;
   a coil mounted within said handpiece;
   a cavity within said handpiece and extending through said coil, said cavity being adapted for removably receiving a scaler insert;
   an oscillating circuit coupled to said coil for providing power to said coil, said oscillating circuit including a transistor oscillator and a transformer coupled to said transistor oscillator; said transformer providing feedback thereto; and
   power supply means coupled to said oscillating circuit such that, when said coil is energized by said oscillating circuit, a scaler insert positioned within said cavity alters the impedance of said coil, and affects the feedback from said transformer to the transistor oscillator to automatically tune the oscillating circuit to cause the insert to vibrate substantially at its resonant frequency.

2. An apparatus as defined by claim 1, wherein the transistor has a base, a collector and an emitter, and wherein the transformer is coupled to the collector and base of said transistor such that the transformer provides feedback from the collector to the base and said transistor operates in response thereto.

3. An apparatus as defined by claim 1, wherein the power supply means comprises a switching regulated power supply.

4. An apparatus as defined by claim 1, wherein the oscillating circuit includes means for setting at least a first and second frequency of oscillation.

5. An apparatus as defined by claim 4, wherein the first frequency of oscillation is about 25 kHz.

6. An apparatus as defined by claim 4, wherein the second frequency of oscillation is about 30 kHz.

7. An apparatus as defined by claim 1, wherein the power supply means further includes a means for temporarily increasing output power of the oscillating circuit to temporarily increase an amplitude of vibration of said scaler insert.

8. An apparatus as defined by claim 7, wherein the means for temporarily increasing output power comprises a push-button switch.

9. An apparatus as defined by claim 1, wherein the oscillating circuit further comprises a protection means for limiting the maximum current permitted to flow in the oscillator circuit to a predetermined value.

10. An apparatus as defined by claim 9, wherein the protection means comprises a current limiting circuit having a transistor, the current limiting circuit having means for detecting current flowing in said oscillator circuit and limiting said current by providing feedback to said transistor.

11. An ultrasonic dental scaler comprising:
    a handpiece adapted for removably receiving a dental scaler insert;
    an energizing coil having a first impedance mounted on said handpiece, the energizing coil being adapted for surrounding a scaler insert removably positioned on said handpiece; and
    means for oscillating a scaler insert, received by said handpiece, the oscillating means comprising a transistor oscillator and a transformer for providing feedback to said transistor oscillator, the oscillating means providing power to the energizing coil, said energizing coil having a second impedance in response to a scaler insert positioned within said energizing coil such that said second impedance affects the feedback from the transformer to the transistor oscillator to thereby automatically tune the oscillating means to vibrate a scaler insert at its resonant frequency.

12. An ultrasonic dental scaler as defined by claim 11, wherein said oscillating means includes a power supply means; and wherein the transistor oscillator provides an attenuated voltage to said energizing coil.

13. An ultrasonic dental scaler as defined by claim 12, wherein said power supply means is a regulated power supply.

14. An ultrasonic dental scaler as defined by claim 13, wherein said regulated power supply is a switching regulated power supply.

15. An ultrasonic dental scaler as defined by claim 11, wherein said power supply means further includes a means for temporarily increasing output power of the oscillating circuit to temporarily increase an amplitude of vibration of said scaler insert.

16. An ultrasonic dental scaler as defined by claim 15, wherein the means for temporarily increasing output voltage comprises a push-button switch which increases output voltage as a percent difference between an original power setting and a full power setting.

17. An ultrasonic dental scaler as defined by claim 11, wherein the oscillating circuit further comprises a protection means for limiting the maximum current permitted to flow in the oscillator circuit to a predetermined value.

18. An ultrasonic dental scaler as defined by claim 17, wherein the protection means comprises a current limiting circuit having a transistor, the current limiting circuit having means for detecting current flowing in said oscillator circuit and limiting said current by providing feedback to said transistor.

19. An ultrasonic dental scaler as defined by claim 11, wherein the transistor has a base, a collector and an emitter, and wherein the transformer is coupled to the collector and base of said transistor such that the transformer provides feedback from the collector to the base and said transistor operated in response thereto.

20. An ultrasonic dental scaler comprising:
    a handpiece adapted for removably receiving a dental scaler insert;
    an energizing coil having a first impedance mounted on said handpiece, the energizing coil being adapted for surrounding a scaler insert removably positioned on said handpiece; and
    means for oscillating the scaler insert, the oscillating means providing power to the energizing coil, said energizing coil having a second impedance in response to a scaler insert positioned within said energizing coil such that said oscillating means is automatically tuned to vibrate a scaler insert at a resonant frequency in response to said second impedance of said energizing coil, and wherein the oscillating means further includes a two position frequency adjustment switch for setting a first and second frequency of oscillation to operate dental scaler inserts having substantially different mechanical resonant frequencies.

21. An ultrasonic dental scaler as defined by claim 20, wherein the first frequency of oscillation is about 25 kHz.

22. An ultrasonic dental scaler as defined by claim 20, wherein the second frequency of oscillation is about 30 kHz.

23. A method of vibrating a dental scaler insert having a scaler tip such that the scaler insert is automatically tuned to vibrate at a resonant frequency to optimize dental scaling procedures, comprising the steps of:

(1) providing a dental scaler device including a handpiece adapted for removably receiving a dental scaler insert, an energizing coil having a first impedance mounted on said handpiece, the energizing coil being adapted for surrounding a scaler insert removably positioned on said handpiece, and means for oscillating the scaler insert by providing power to the energizing coil, the oscillating means comprising a transistor oscillator and a transformer, the transformer providing feedback to the transistor oscillator; and (2) inserting a dental scaler insert within the energizing coil such that the energizing coil has a second impedance in response to the scaler insert whereby the oscillating means is automatically tuned to the resonant frequency of oscillation of the scaler insert in response to the second impedance of the energizing coil affecting the transformer feedback to the transistor oscillator to thereby provide a desired vibration at the resonant frequency of the scaler insert for dental scaling procedures.

24. A method of vibrating a dental scaler insert as defined by claim 23, further including the steps prior to step (2) of:

(1a) providing a means for setting at least a first and second frequency oscillation of said oscillating means;

(1b) selecting a dental scaler insert having a desired resonant frequency of oscillation associated therewith; and (1c) positioning said setting means to correspond to the selected resonant frequency of oscillation of the scaler insert.

25. A method of vibrating a dental scaler insert as defined by claim 24, further including steps subsequent to step (2) of:

(3) providing a means for temporarily increasing an amplitude of vibration of said dental scaler insert tip; and (4) operating said means for temporarily increasing the amplitude of vibration of the dental scaler insert tip to dislodge stubborn calculus from a patient's teeth.

26. An ultrasonic dental scaler comprising:

a handpiece adapted for removably receiving a magnetostrictive dental scaler insert;

energizing means on the handpiece selectively positioned with respect to a dental scaler insert received by the handpiece; and means for oscillating the scaler insert, the oscillating means including a transistor oscillator and a transformer, the transformer coupled to and providing feedback to said transistor oscillator, the oscillating means providing power to the energizing means, the energizing means being responsive to the selective positioning of the dental scaler insert received by the handpiece such that the oscillating means is automatically tuned to vibrate said dental scaler insert at a resonant frequency in response to said energizing means affecting said transformer feedback to the transistor oscillator.

27. A method of vibrating a dental scaler insert having a scaler tip comprising the steps of:

(1) providing a dental scaler device including a handpiece adapted for removable receiving a dental scaler insert, energizing means on the handpiece selectively positioned with respect to a dental scaler insert received by the handpiece and means for oscillating the scaler insert, the oscillating means providing power to the energizing means;

(2) providing a means for setting at least a first and second frequency of oscillation;

(3) selecting a dental scaler insert having a desired resonant frequency of oscillation associated therewith;

(4) positioning said setting means to correspond to the selected resonant frequency of oscillation of the scaler insert; and (5) inserting the dental scaler insert within the handpiece whereby the energizing means is responsive to the selective positioning of the dental scaler insert received by the handpiece such that the oscillating means is automatically tuned to vibrate said dental scaler insert at a resonant frequency in response to said energizing means.

* * * * *